(12) United States Patent
Oka et al.

(10) Patent No.: US 10,450,266 B2
(45) Date of Patent: Oct. 22, 2019

(54) SULFONATE COMPOUND, PHOTOACID GENERATOR, AND RESIN COMPOSITION FOR PHOTOLITHOGRAPHY

(71) Applicant: SAN-APRO LIMITED, Kyoto-shi, Kyoto (JP)

(72) Inventors: Masaaki Oka, Kyoto (JP); Yuji Nakamura, Kyoto (JP)

(73) Assignee: SAN-APRO LIMITED, Kyoto-shi (JP)

( * ) Notice: Subject to any disclaimer, the term of this patent is extended or adjusted under 35 U.S.C. 154(b) by 0 days.

(21) Appl. No.: 15/519,308

(22) PCT Filed: Oct. 13, 2015

(86) PCT No.: PCT/JP2015/005178
§ 371 (c)(1),
(2) Date: Apr. 14, 2017

(87) PCT Pub. No.: WO2016/072049
PCT Pub. Date: May 12, 2016

(65) Prior Publication Data
US 2017/0233336 A1    Aug. 17, 2017

(30) Foreign Application Priority Data

Nov. 7, 2014    (JP) ................................. 2014-226935

(51) Int. Cl.
| | |
|---|---|
| *C07C 309/65* | (2006.01) |
| *C07C 309/64* | (2006.01) |
| *C09K 3/00* | (2006.01) |
| *G03F 7/004* | (2006.01) |
| *G03F 7/038* | (2006.01) |
| *C07C 309/73* | (2006.01) |
| *C07D 311/12* | (2006.01) |
| *C08G 59/68* | (2006.01) |

(52) U.S. Cl.
CPC .......... *C07C 309/65* (2013.01); *C07C 309/64* (2013.01); *C07C 309/73* (2013.01); *C07D 311/12* (2013.01); *C09K 3/00* (2013.01); *G03F 7/004* (2013.01); *G03F 7/0045* (2013.01); *G03F 7/038* (2013.01); *C08G 59/68* (2013.01)

(58) Field of Classification Search
CPC ........... G03F 7/038; G03F 7/004; C09K 3/00; C08G 59/68; C07C 309/64
USPC ........................................................ 549/285
See application file for complete search history.

(56) References Cited

U.S. PATENT DOCUMENTS

| | | | |
|---|---|---|---|
| 4,371,605 A | 2/1983 | Renner | |
| 5,002,853 A * | 3/1991 | Aoai | G03F 7/039 430/270.1 |
| 5,409,930 A | 4/1995 | Spada et al. | |
| 2017/0168393 A1 * | 6/2017 | Sugihara | C08F 220/28 |

FOREIGN PATENT DOCUMENTS

| | | |
|---|---|---|
| GB | 1516511 A | 7/1978 |
| JP | 50-151997 A | 12/1975 |
| JP | 1-293339 A | 11/1989 |
| JP | 2-100055 A | 4/1990 |
| JP | 6-67433 A | 3/1994 |
| JP | 9-118663 A | 5/1997 |
| JP | 9-185160 A | 7/1997 |
| JP | 9-239945 A | 9/1997 |
| JP | 10-16423 A | 1/1998 |
| JP | 10-80994 A | 3/1998 |
| JP | 10-142777 A | 5/1998 |
| JP | 10-213899 A | 8/1998 |
| JP | 10-228109 A | 8/1998 |

(Continued)

OTHER PUBLICATIONS

International Preliminary Report on Patentability, dated May 9, 2017, issued in international Application No. PCT/JP2015/005178 (9 pages).*
Okumoto; J. Pharm. Dyn. 1979, 2, 397-402. (Year: 1979).*
Hoffman; J. Org. Chem. 1994, 59, 13, 3530-3539. (Year: 1994).*
Chemical Abstracts STN Registry Database; record for RN1243852-81-4, entered on Sep. 30, 2010. (Year: 2010).*
Chemical Abstracts STN Registry Database record for RN 1027168-87-1, entered on Jun. 11, 2008. (Year: 2008).*
Chemical Abstracts STN Registry Database; record for RN1027984-84-4, 1,1,1-Trifluoromethanesulfonic acid, methyl(1-naphthalenylcarbonyl)azanyl ester, entered into STN on Jun. 13, 2008. (Year: 2008).*

(Continued)

*Primary Examiner* — Daniel R Carcanague
(74) *Attorney, Agent, or Firm* — Westerman, Hattori, Daniels & Adrian, LLP

(57) ABSTRACT

Provided are: a non-ionic photoacid generator containing a sulfonate compound having a high photosensitivity to i lines, exhibiting excellent heat-resistance stability, and exhibiting excellent solubility in a hydrophobic material; and a resin composition for photolithography containing the same. The present invention is a sulfonate compound characterized by being represented by general formula (1).
[In formula (1), R1 represents an aryl group having 6 to 18 carbon atoms or a heterocyclic hydrocarbon group having 4 to 20 carbon atoms. R2 represents a hydrogen atom, an alkyl group having 1 to 18 carbon atoms, an alkenyl group having 2 to 18 carbon atoms, an alkynyl group having 2 to 18 carbon atoms, or an aryl group having 6 to 18 carbon atoms. R3 represents a hydrocarbon group having 1 to 18 carbon atoms (in which some or all hydrogen atoms may be substituted with fluorine).]

(1)

$$R1-\underset{\underset{R2}{|}}{\underset{N}{C}}(=O)-O-\underset{\underset{O}{||}}{\overset{\overset{O}{||}}{S}}-R3$$

6 Claims, No Drawings

(56) References Cited

FOREIGN PATENT DOCUMENTS

JP 11-38630 A 2/1999
JP 2007-31351 A 2/2007

OTHER PUBLICATIONS

Okawara et al., Convenient Syntheses of I-Acyl-2-alkylhydrazines, Synthesis, Feb. 1987, No. 2, pp. 183-184 (3 pages, including cover page), cited in ISR.
Misra et al, Tosylation of N-Acyl-O-alkylhydroxylamines: Part III—Synthesis of Tosyl O-Alkyl-arylcarbohydroxamates, Indian Journal of Chemistry, vol. 15B, Jan. 1977, pp. 49-50 (3 pages, including cover page), cited in ISR.
Hoffman et al., Generation of N-Acyl Iminium Ions from Ionization-Rearrangement Reactions of N-Triflyloxy Amides, Tetrahedron Letters, vol. 35, No. 20, 1994, pp. 3231-3234 (4 pages), cited in ISR.
Hoffman et al., A Facile Preparation of N-(Isopropoxyalkyl) Amides by Generation and Trapping of N-Acylimlnium ons from Ionization-Rearrangement Reactions of N-Triflyloxy Amides, Journal of Organic Chemistry, vol. 59, No. 13, 1994, pp. 3530-3539 (10 pages), cited in ISR.
Gessner et al., Internal Mobility in the Ion Pairs during Aromatic Rearrangement of O-Sulfonyl-N-phenylhydroxylamines, Chemische Berichte, vol. 115, No. 8, 1982, pp. 2865-2871 (8 pages, including cover page), w/ English abstract, cited in ISR.

Kaluza et al., the Light-Catalysed Hydrolytic Reactions of 2,4-Dinitrobenzenesulphenyl Chloride with a Note on the Carbonyl Infrared Absorption of Ester and Amide Derivatives of N-phenylhydroxylamine, Journal of the South African Chemical Institute, 1960, vol. XIII, pp. 89-96 (9 pages, including cover page), cited in ISR.
Przychodzen et al, On the Reaction of Bis(phosphothioyl)disulfanes with Hydroxamic Acids, Part I: Ionic versus Radical Reaction Pathways, Heteroatom Chemistry, vol. 19, No. 3, 2008, pp. 271-282 (13 pages, including cover page), cited in ISR.
Trunov et al., Rearrangement of N-(phenylsulfoxy)benzamide, Zhumal Organicheskoi Khimii, vol. 11, No. 5, 1975, pp. 1136-1137 (3 pages, including cover page), cited in ISR.
Banks et al., The Reaction of N-Alkylhydroxamic Acids with Sulphinyl Chlorides, Journal of the Chemical Society, Perkin Transactions II, No. 8, 1986, pp. 1211-1216 (7 pages, including cover page), cited in ISR.
Database: ChemSpider (Chemzoo, Inc.), Entered STN: Jun. 13, 2008, accession No. 1027984-84-4, Registry [online], [retrieved on Dec. 14, 2015], retrieved from: STN, cited in ISR.
Chemical Library Supplier: Ambinter, Entered STN: Nov. 28, 2008, accession No. 304645-12-3 Registry [online], [retrieved on Dec. 14, 2015], retrieved from: STN, cited in ISR.
International Search Report dated Dec. 28, 2015, issued in counterpart International Application No. PCT/JP2015/005178 (4 pages).

* cited by examiner

SULFONATE COMPOUND, PHOTOACID GENERATOR, AND RESIN COMPOSITION FOR PHOTOLITHOGRAPHY

TECHNICAL FIELD

The present invention relates to a sulfonate compound, a photoacid generator and a resin composition for photolithography. More particularly, it relates to a non-ionic photoacid generator suitable for allowing ultraviolet rays (i-line) to act on the photoacid generator to generate a strong acid, and a resin composition for photolithography containing the same.

BACKGROUND ART

In a field of fine processing typified by semiconductor manufacturing, a photolithography process in which i-line with a wavelength of 365 nm is used as exposure light has hitherto been widely used.

As the resist material used in the photolithography process, for example, a resin composition containing a polymer having a carboxylic acid tert-butyl ester group or a phenolic tert-butyl carbonate group and a photoacid generator has been used. As the photoacid generator, ionic photoacid generators such as a triaryl sulfonium salt (Patent Document 1) and a phenacyl sulfonium salt having a naphthalene skeleton (Patent Document 2) and non-ionic acid generators such as an acid generator having an oximesulfonate structure (Patent Document 3) and an acid generator having a sulfonyldiazomethane structure (Patent Document 4) have been known. By allowing this resist material to be irradiated with ultraviolet rays, the photoacid generator is decomposed to generate a strong acid. Furthermore, by being subjected to post exposure baking (PEB), a tert-butyl ester group or a tert-butyl carbonate group is dissociated from the polymer by virtue of this strong acid, a carboxylic acid or a phenolic hydroxyl group is formed, and a part irradiated with ultraviolet rays becomes readily-soluble in an alkali developing solution. This phenomenon is utilized to perform pattern formation.

However, as the photolithography process becomes finer processing, since the influence of swelling becomes greater when the pattern of a light-unexposed part is swelled due to an alkali developing solution, it is necessary to suppress the resist material from being swelled.

For the purpose of solving these problems, there has been proposed a method of suppressing the swelling of the resist material by allowing an alicyclic skeleton, a fluorine-containing skeleton, or the like to be contained in a polymer in the resist material to make the polymer hydrophobic.

However, with regard to the ionic photoacid generator, since the compatibility against a hydrophobic material containing an alicyclic skeleton, a fluorine-containing skeleton, and the like is insufficient, there is a problem that sufficient resist performance is not exerted since the phase separation occurs in the resist material and the pattern formation results in failure. On the other hand, although the non-ionic photoacid generator is satisfactory in compatibility against a hydrophobic material, there are a problem that the sensitivity to i-line is insufficient and a problem that the allowance range is narrow since the heat-resistant stability is insufficient and the photoacid generator is decomposed by post exposure baking (PEP).

PRIOR ART DOCUMENTS

Patent Documents

Patent Document 1: JP-A-50-151997
Patent Document 2: JP-A-9-118663
Patent Document 3: JP-A-06-67433
Patent Document 4: JP-A-10-213899

SUMMARY OF THE INVENTION

Problems to be Solved by the Invention

Accordingly, an object of the present invention is to provide a non-ionic photoacid generator having high photosensitivity to i-line, being excellent in heat-resistant stability and being excellent in solubility to a hydrophobic material.

Solutions to the Problems

The present inventors have conducted studies in view of achieving the above-described object, and as a result, the present invention has been completed.

That is, the present invention is directed to a sulfonate compound, being represented by the general formula (1).

[Chemical 1]

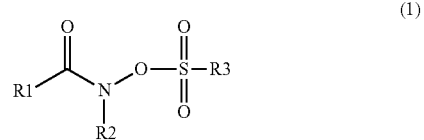

(1)

[In formula (1), R1 represents an aryl group having 6 to 18 carbon atoms or a heterocyclic hydrocarbon group having 4 to 20 carbon atoms. R2 represents a hydrogen atom, an alkyl group having 1 to 18 carbon atoms, an alkenyl group having 2 to 18 carbon atoms, an alkynyl group having 2 to 18 carbon atoms, or an aryl group having 6 to 18 carbon atoms. R3 represents a hydrocarbon group having 1 to 18 carbon atoms (in which some or all hydrogen atoms may be substituted with fluorine).]

EFFECTS OF THE INVENTION

The sulfonate compound according to the present invention is a non-ionic compound, a non-ionic photoacid generator (A) containing the compound is a non-ionic photoacid generator, and the non-ionic photoacid generator (A) is excellent in compatibility with a hydrophobic material as compared to an ionic photoacid generator. Moreover, since the non-ionic photoacid generator (A) has an imide skeleton which is an i-line absorbing moiety, the non-ionic photoacid generator (A) can be easily decomposed by being irradiated with i-line to generate sulfonic acid which is a strong acid. Furthermore, since the non-ionic photoacid generator (A) has an imide skeleton, the non-ionic photoacid generator (A) is excellent in heat-resistant stability.

As such, the resin composition (Q) for photolithography containing the non-ionic photoacid generator (A) according to the present invention is highly sensitive to i-line, and moreover, is excellent in usability since the allowance range at the time of post exposure baking (PEE) is wide.

MODE FOR CARRYING OUT THE INVENTION

The sulfonate compound according to the present invention is represented by the above general formula (1).

In formula (1), R1 is an aryl group having 6 to 18 carbon atoms or a heterocyclic hydrocarbon group having 4 to 20 carbon atoms.

Examples of the aryl group having 6 to 18 carbon atoms as said R1 include a phenyl group, a naphthyl group, an anthracenyl group, a biphenyl group, a phenanthryl group, a pyrenyl group, and the like.

Examples of the heterocyclic hydrocarbon group having 4 to 20 carbon atoms as said R1 include a furyl group, a thienyl group, a pyranyl group, a pyridyl group, a thiazole group, a coumarinyl group, a carbazole group, a thioxanthonyl group, and the like.

The aryl group having 6 to 18 carbon atoms and the heterocyclic hydrocarbon group having 4 to 20 carbon atoms as said R1s may have a substituent (T). Examples of the substituent (T) include an alkyl group, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, and a halogen atom. One kind of the substituent (T) or two or more kinds thereof may be employed.

Examples of the alkyl group include a linear alkyl group having 1 to 18 carbon atoms (methyl, ethyl, n-propyl, n-butyl, n-pentyl, n-octyl, n-decyl, n-dodecyl, n-tetradecyl, n-hexadecyl, n-octadecyl, or the like), a branched-chain alkyl group having 1 to 18 carbon atoms (isopropyl, isobutyl, sec-butyl, tert-butyl, isopentyl, neopentyl, tert-pentyl, isohexyl, or isooctadecyl), a cycloalkyl group having 3 to 18 carbon atoms (cyclopropyl, cyclobutyl, cyclopentyl, cyclohexyl, 4-decylcyclohexyl, or the like), a linear or branched fluoroalkyl group having 1 to 3 carbon atoms (a trifluoromethyl, pentafluoroethyl, or heptafluorobutyl group, or the like) and the like.

Examples of the alkoxy group include a linear or branched-chain alkoxy group having 1 to 18 carbon atoms (methoxy, ethoxy, propoxy, isopropoxy, butoxy, isobutoxy, sec-butoxy, tert-butoxy, hexyloxy, decyloxy, dodecyloxy, octadecyloxy, or the like) and the like.

Examples of the alkylcarbonyl group include a linear or branched-chain alkylcarbonyl group having 2 to 18 carbon atoms (including the carbonyl carbon) (acetyl, propionyl, butanoyl, 2-methylpropionyl, heptanoyl, 2-methylbutanoyl, 3-methylbutanoyl, octanoyl, decanoyl, dodecanoyl, octadecanoyl, or the like) and the like.

Examples of the arylcarbonyl group include an arylcarbonyl group having 7 to 11 carbon atoms (including the carbonyl carbon) (benzoyl, naphthoyl, or the like) and the like.

Examples of the alkoxycarbonyl group include a linear or branched-chain alkoxycarbonyl group having 2 to 19 carbon atoms (including the carbonyl carbon) (methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, octyloxycarbonyl, tetradecyloxycarbonyl, octadecyloxycarbonyl, or the like) and the like.

Examples of the aryloxycarbonyl group include an aryloxycarbonyl group having 7 to 11 carbon atoms (including the carbonyl carbon) (phenoxycarbonyl, naphthoxycarbonyl, or the like) and the like.

Examples of the arylthiocarbonyl group include an arylthiocarbonyl group having 7 to 11 carbon atoms (including the carbonyl carbon) (phenylthiocarbonyl, naphthoxythiocarbonyl, or the like) and the like.

Examples of the acyloxy group include a linear or branched-chain acyloxy group having 2 to 19 carbon atoms (acetoxy, ethylcarbonyloxy, propylcarbonyloxy, isopropylcarbonyloxy, butylcarbonyloxy, isobutylcarbonyloxy, sec-butylcarbonyloxy, tert-butylcarbonyloxy, octylcarbonyloxy, tetradecylcarbonyloxy, octadecylcarbonyloxy, or the like) and the like.

Examples of the arylthio group include an arylthio group having 6 to 20 carbon atoms (phenylthio, 2-methylphenylthio, 3-methylphenylthio, 4-methylphenylthio, 2-chlorophenylthio, 3-chlorophenylthio, 4-chlorophenylthio, 2-bromophenylthio, 3-bromophenylthio, 4-bromophenylthio, 2-fluorophenylthio, 3-fluorophenylthio, 4-fluorophenylthio, 2-hydroxyphenylthio, 4-hydroxyphenylthio, 2-methoxyphenylthio, 4-methoxyphenylthio, 1-naphthylthio, 2-naphthylthio, 4-[4-(phenylthio)benzoyl]phenylthio, 4-[4-(phenylthio)phenoxy]phenylthio, 4-[4-(phenylthio)phenyl]phenylthio, 4-(phenylthio)phenylthio, 4-benzoylphenylthio, 4-benzoyl-2-chlorophenylthio, 4-benzoyl-3-chlorophenylthio, 4-benzoyl-3-methylthiophenylthio, 4-benzoyl-2-methylthiophenylthio, 4-(4-methylthiobenzoyl)phenylthio, 4-(2-methylthiobenzoyl)phenylthio, 4-(p-methylbenzoyl)phenylthio, 4-(p-ethylbenzoyl)phenylthio, 4-(p-isopropylbenzoyl)phenylthio, 4-(p-tert-butylbenzoyl)phenylthio, or the like) and the like.

Examples of the alkylthio group include a linear or branched-chain alkylthio group having 1 to 18 carbon atoms (methylthio, ethylthio, propylthio, isopropylthio, butylthio, isobutylthio, sec-butylthio, tert-butylthio, pentylthio, isopentylthio, neopentylthio, tert-pentylthio, octylthio, decylthio, dodecylthio, isooctadecylthio, or the like) and the like.

Examples of the aryl group include an aryl group having 6 to 10 carbon atoms (phenyl, tolyl, dimethylphenyl, naphthyl, or the like) and the like.

Examples of the heterocyclic hydrocarbon group include a heterocyclic hydrocarbon group having 4 to 20 carbon atoms (thienyl, furanyl, pyranyl, pyrrolyl, oxazolyl, thiazolyl, pyridyl, pyrimidyl, pyrazinyl, indolyl, benzofuranyl, benzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, dibenzothienyl, xanthonyl, thioxanthonyl, dibenzofuranyl, or the like) and the like.

Examples of the aryloxy group include an aryloxy group having 6 to 10 carbon atoms (phenoxy, naphthyloxy, or the like) and the like.

Examples of the alkylsulfinyl group include a linear or branched-chain alkylsulfinyl group having 1 to 18 carbon atoms (methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, isopentylsulfinyl, neopentylsulfinyl, tert-pentylsulfinyl, octylsulfinyl, isooctadecylsulfinyl, or the like) and the like.

Examples of the arylsulfinyl group include an arylsulfinyl group having 6 to 10 carbon atoms (phenylsulfinyl, tolylsulfinyl, naphthylsulfinyl, or the like) and the like.

Examples of the alkylsulfonyl group include a linear or branched-chain alkylsulfonyl group having 1 to 18 carbon atoms (methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, neopentylsulfonyl, tert-pentylsulfonyl, octylsulfonyl, octadecylsulfonyl, or the like) and the like.

Examples of the arylsulfonyl group include an arylsulfonyl group having 6 to 10 carbon atoms {phenylsulfonyl, tolylsulfonyl (a tosyl group), naphthylsulfonyl, or the like} and the like.

Examples of the halogen atom include a fluorine atom, a chlorine atom, a bromine atom, an iodine atom, and the like.

Among these substituents (T), from the viewpoints of the ease of synthesis, the absorption wavelength region and the heat-resistant stability, a hydroxy group, an alkyl group, an alkoxy group, an arylcarbonyl group, an aryloxycarbonyl group, an arylthio group, an aryl group, an aryloxy group, an arylsulfinyl group, an arylsulfonyl group, a fluorine atom, and a chlorine atom are preferred, and a hydroxy group, an alkoxy group, an arylthio group, a fluorine atom, and a chlorine atom are especially preferred.

Among R1s, preferred are a phenyl group, a naphthyl group, an anthracenyl group, a biphenyl group, a phenanthryl group, a pyrenyl group, a furyl group, a thienyl group, a pyranyl group, a pyridyl group, a thiazole group, a coumarinyl group, a carbazole group, and a thioxanthonyl group, and further preferred are a phenyl group, a naphthyl group, an anthracenyl group, a coumarinyl group, and a thioxanthonyl group.

In formula (1), R2 is a hydrogen atom, an alkyl group having 1 to 18 carbon atoms, an alkenyl group having 2 to 18 carbon atoms, an alkynyl group having 2 to 18 carbon atoms, or an aryl group having 6 to 18 carbon atoms.

Examples of the alkyl group having 1 to 18 carbon atoms as said R2 include a linear alkyl group having 1 to 18 carbon atoms (methyl, ethyl, n-propyl, n-butyl, n-pentyl, n-octyl, n-decyl, n-dodecyl, n-tetradecyl, n-hexadecyl, n-octadecyl, or the like), a branched-chain alkyl group having 1 to 18 carbon atoms (isopropyl, isobutyl, sec-butyl, tert-butyl, isopentyl, neopentyl, tert-pentyl, isohexyl, or isooctadecyl), a cycloalkyl group having 3 to 18 carbon atoms (cyclopropyl, cyclobutyl, cyclopentyl, cyclohexyl, 4-decylcyclohexyl, or the like), a linear or branched fluoroalkyl group having 1 to 3 carbon atoms (a trifluoromethyl, pentafluoroethyl, or heptafluorobutyl group, or the like) and the like.

Examples of the alkenyl group having 2 to 18 carbon atoms as said R2 include a linear or branched one such as vinyl, allyl, 1-propenyl, isopropenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-2-butenyl, 3-methyl-2-butenyl, 1,2-dimethyl-1-propenyl, 1-decenyl, 2-decenyl, 8-decenyl, 1-dodecenyl, 2-dodecenyl, and 10-dodecenyl.

Examples of the alkynyl group having 2 to 18 carbon atoms as said R2 include a linear or branched one such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1,2-dimethyl-2-propynyl, 1-decynyl, 2-decynyl, 8-decynyl, 1-dodecynyl, 2-dodecynyl, and 10-dodecynyl.

Examples of the aryl group having 6 to 18 carbon atoms as said R2 include phenyl, tolyl, dimethylphenyl, naphthyl, anthracenyl, biphenyl, pentafluorophenyl, and the like.

Among R2 s, preferred is a hydrogen atom or an alkyl group having 1 to 18 carbon atoms, and especially preferred is a hydrogen atom, a methyl group, an ethyl group, an n-propyl group, an isopropyl group, an n-butyl group, a sec-butyl group, or a tert-butyl group.

R3, which is an essential functional group for allowing the sulfonic acid ester moiety to be decomposed by ultraviolet ray irradiation, is a hydrocarbon group having 1 to 18 carbon atoms (in which some or all hydrogen atoms may be substituted with fluorine) which may have a substituent. As the substituent, one exemplified as the substituent (T) can be used. Examples of the hydrocarbon group having 1 to 18 carbon atoms include an alkyl group, an aryl group, and a heterocyclic hydrocarbon group.

Examples of the alkyl group include a linear alkyl group having 1 to 18 carbon atoms (methyl, ethyl, n-propyl, n-butyl, n-pentyl, n-octyl, n-decyl, n-dodecyl, n-tetradecyl, n-hexadecyl, n-octadecyl, or the like), a C1-18 branched-chain alkyl group having 1 to 18 carbon atoms (isopropyl, isobutyl, sec-butyl, tert-butyl, isopentyl, neopentyl, tert-pentyl, isohexyl, or isooctadecyl), a cycloalkyl group having 3 to 18 carbon atoms (cyclopropyl, cyclobutyl, cyclopentyl, cyclohexyl, 4-decylcyclohexyl, 10-camphoryl, or the like) and the like.

Examples of the aryl group include an aryl group having 6 to 10 carbon atoms (phenyl, tolyl, dimethylphenyl, naphthyl, pentafluorophenyl, or the like) and the like.

Examples of the heterocyclic hydrocarbon group include a heterocyclic hydrocarbon group having 4 to 20 carbon atoms (thienyl, furanyl, pyranyl, pyrrolyl, oxazolyl, thiazolyl, pyridyl, pyrimidyl, pyrazinyl, indolyl, benzofuranyl, benzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, dibenzothienyl, xanthonyl, thioxanthonyl, dibenzofuranyl, or the like) and the like.

Examples of a group in which some or all hydrogen atoms of the hydrocarbon group having 1 to 18 carbon atoms which may have a substituent are substituted with fluorine include a linear alkyl group (RF1), a branched-chain alkyl group (RF2), a cycloalkyl group (RF3), and an aryl group (RF4), which are represented by CxFv, in which hydrogen atoms are substituted with fluorine atoms.

Examples of the linear alkyl group (RF1) in which hydrogen atoms are substituted with fluorine atoms include a trifluoromethyl group ($x=1$, $y=3$), a pentafluoroethyl group ($x=2$, $y=5$), a nonafluorobutyl group ($x=4$, $y=9$), a perfluorohexyl group ($x=6$, $y=13$), a perfluorooctyl group ($x=8$, $y=17$) and the like.

Examples of the branched-chain alkyl group (RF2) in which hydrogen atoms are substituted with fluorine atoms include a perfluoroisopropyl group ($x=3$, $y=7$), a perfluoro-tert-butyl group ($x=4$, $y=9$), a perfluoro-2-ethylhexyl group ($x=8$, $y=17$) and the like.

Examples of the cycloalkyl group (RF3) in which hydrogen atoms are substituted with fluorine atoms include a perfluorocyclobutyl group ($x=4$, $y=7$), a perfluorocyclopentyl group ($x=5$, $y=9$), a perfluorocyclohexyl group ($x=6$, $y=11$), a perfluoro(1-cyclohexyl)methyl group ($x=7$, $y=13$) and the like.

Examples of the aryl group (RF4) in which hydrogen atoms are substituted with fluorine atoms include a pentafluorophenyl group ($x=6$, $y=5$), a 3-trifluoromethyltetrafluorophenyl group ($x=7$, $y=7$) and the like.

Among R3s, preferred is a linear alkyl group having 1 to 18 carbon atoms, a branched-chain alkyl group having 1 to 18 carbon atoms, a cycloalkyl group having 3 to 18 carbon atoms, an aryl group having 6 to 10 carbon atoms, or a heterocyclic hydrocarbon group having 4 to 20 carbon atoms, and especially preferred is a methyl group, an ethyl group, an n-propyl group, an n-butyl group, an n-pentyl group, an n-octyl group, an n-decyl group, an n-dodecyl group, an isopropyl group, an isobutyl group, a sec-butyl group, a tert-butyl group, an isopentyl group, a neopentyl group, a tert-pentyl group, an isohexyl group, an isooctadecyl group, a cyclopropyl group, a cyclobutyl group, a cyclopentyl group, a cyclohexyl group, 4-decylcyclohexyl, or 10-camphoryl.

From the viewpoints of the ease of synthesis, the adjustment of the absorption wavelength region and the heat-resistant stability, preferred specific examples of a sulfonate compound represented by general formula (1) include the following. In this connection, in the structural formula of the compound, N—, O— and — represent N—CH$_3$, O—CH$_3$ and —CH$_3$, respectively. The same holds true for description below.

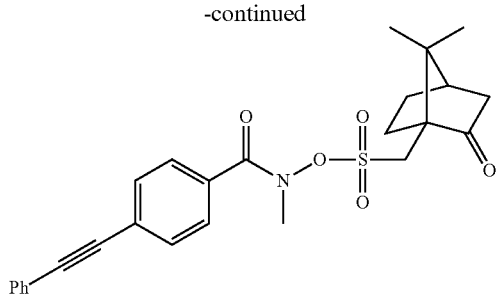

-continued
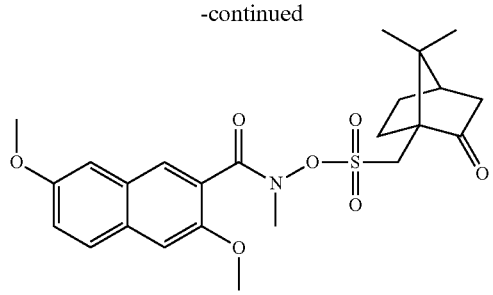
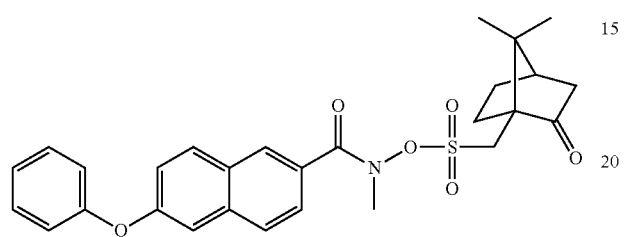
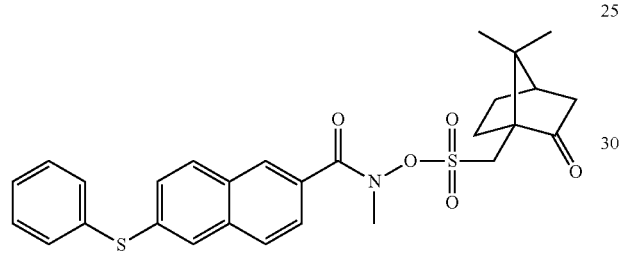
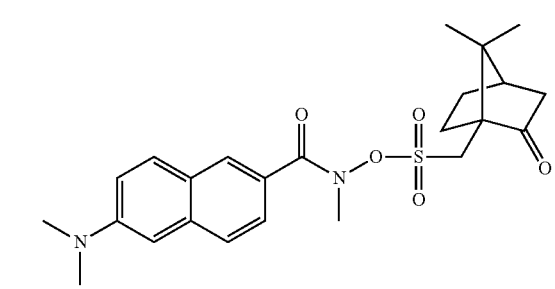
[Chemical 4]
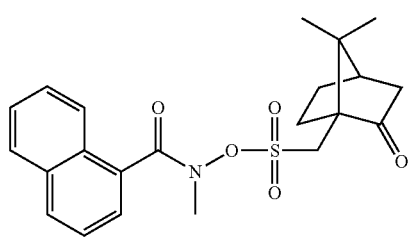
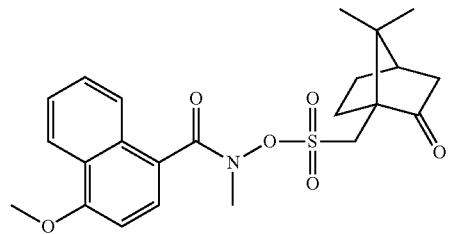
-continued
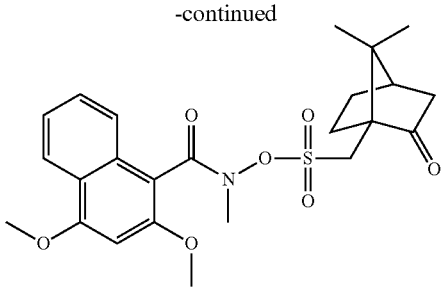
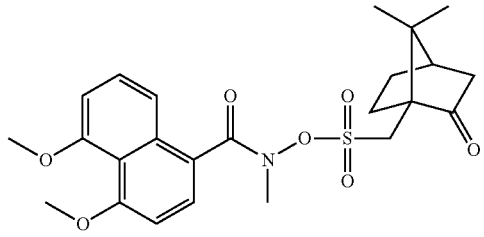
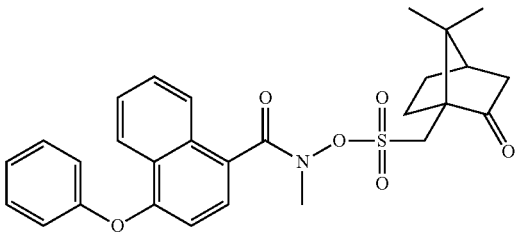
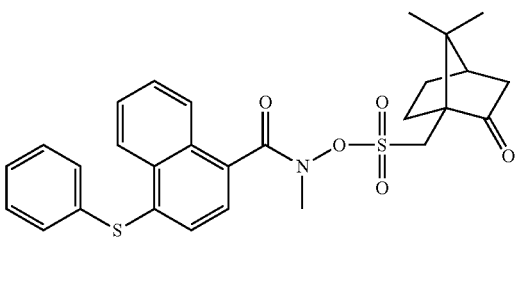
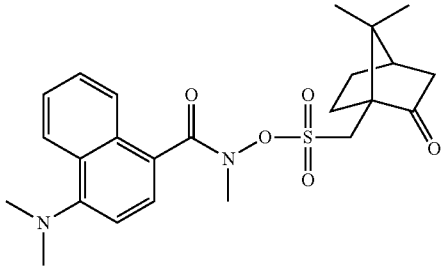
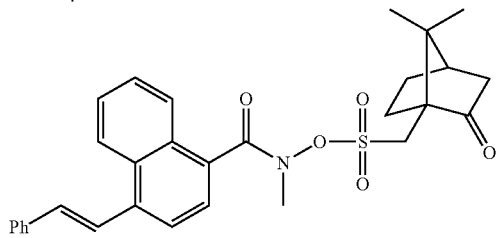

11
-continued
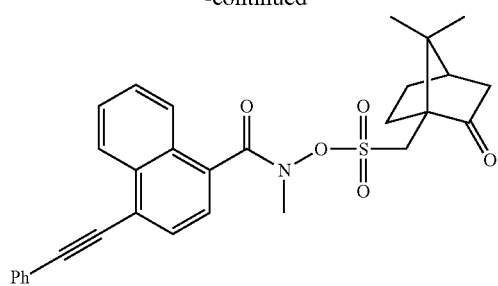
[Chemical 5]
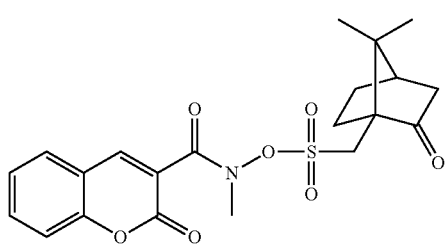
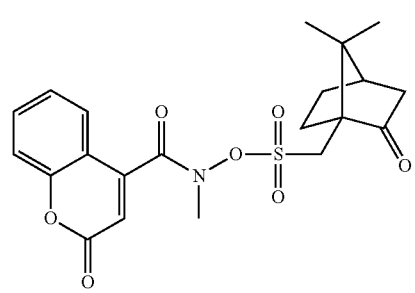
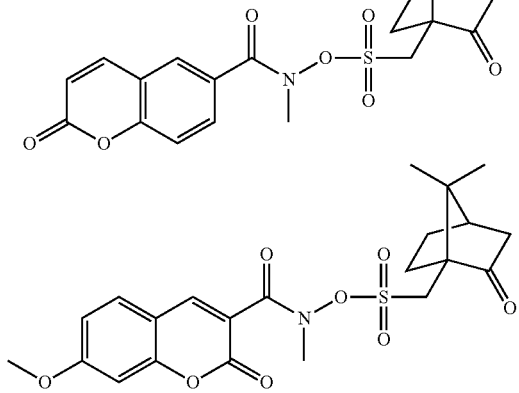
12
-continued
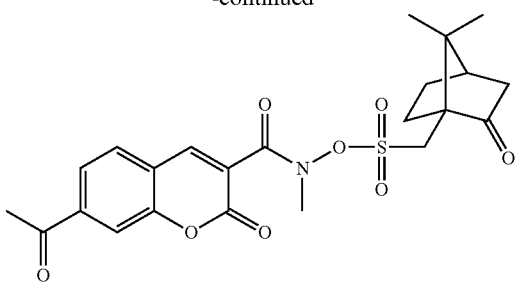
[Chemical 6]
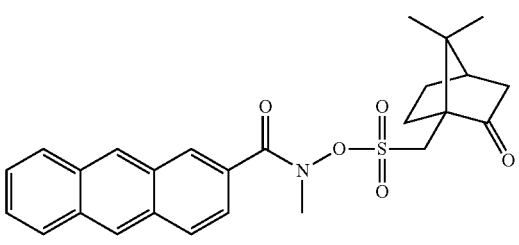
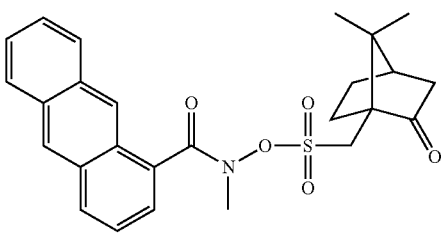
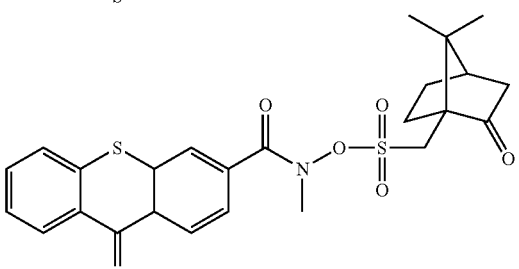

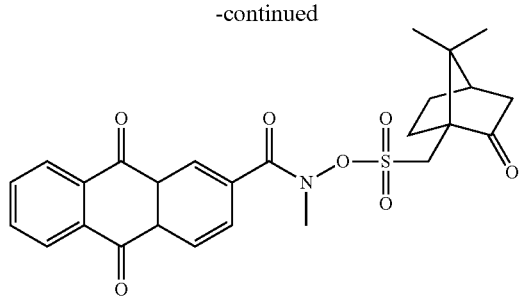
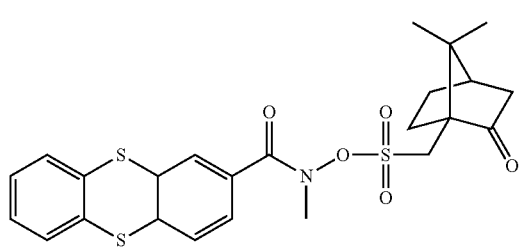
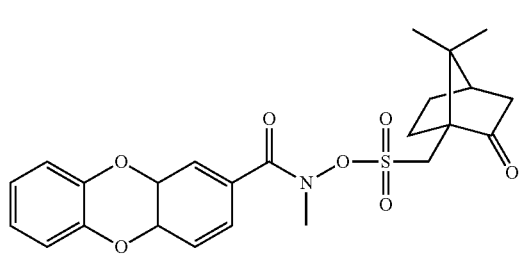
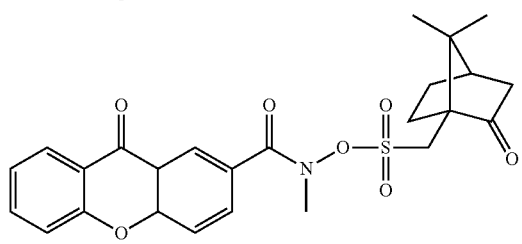
[Chemical 7]
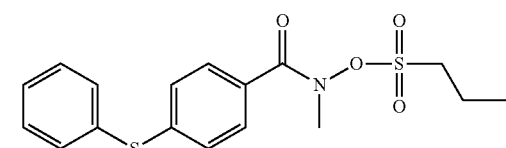
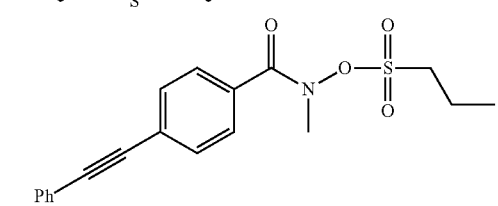
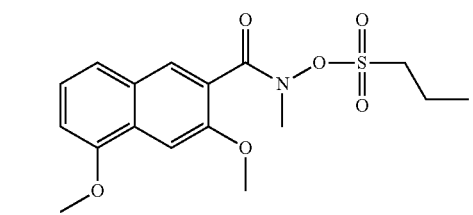
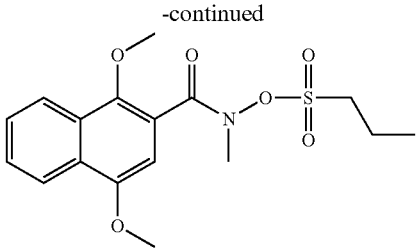
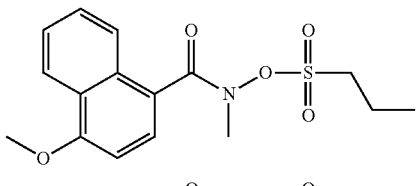
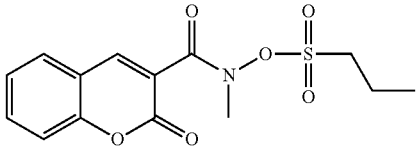
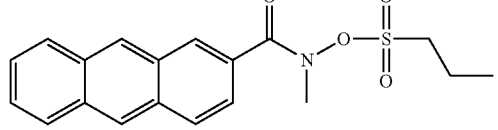
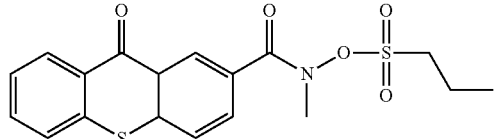
[Chemical 8]
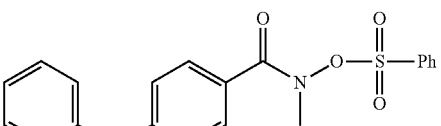
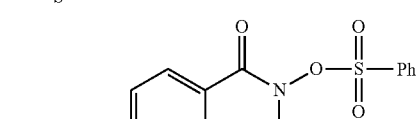
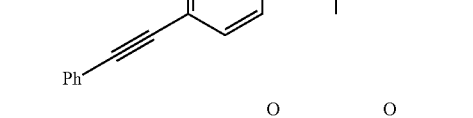
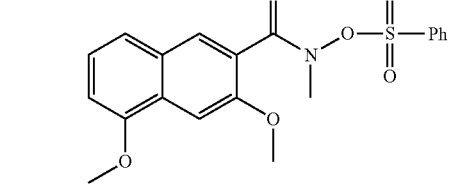

-continued

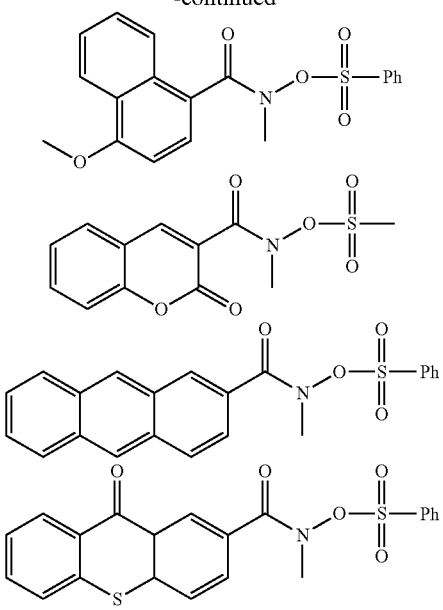

Although the synthetic method of the sulfonate compound according to the present invention is not particularly limited as long as the aimed product is synthesized, for example, the sulfonate compound can be synthesized by the reaction of an N-hydroxyimide compound (P1) as a precursor and a sulfonic acid anhydride shown by $(R3-SO_2)_2O$ or the reaction of a salt of an N-hydroxyimide compound (P1) and sulfonic acid chloride shown by $R3-SO_2Cl$.

The non-ionic photoacid generator (A) according to the present invention may be previously dissolved in a solvent not inhibiting the reaction in order to facilitate the dissolution thereof in a resist material.

Examples of the solvent include a carbonate (propylene carbonate, ethylene carbonate, 1,2-butylene carbonate, dimethyl carbonate, diethyl carbonate, and the like); an ester (ethyl acetate, ethyl lactate, β-propiolactone, β-butyrolactone, γ-butyrolactone, δ-valerolactone, ε-caprolactone and the like); an ether (ethylene glycol monomethyl ether, propylene glycol monoethyl ether, diethylene glycol monombutyl ether, dipropylene glycol dimethyl ether, triethylene glycol diethyl ether, tripropylene glycol dibutyl ether, and the like); an ether ester (ethylene glycol monomethyl ether acetate, propylene glycol monoethyl ether acetate, diethylene glycol monombutyl ether acetate, and the like) and the like.

In the case of using a solvent, the proportion of the solvent used is preferably 15 to 1000 parts by weight, and further preferably 30 to 500 parts by weight, relative to 100 parts by weight of the photoacid generator according to the present invention.

Since the resin composition (Q) for photolithography according to the present invention includes the non-ionic photoacid generator (A) as an essential component, by performing ultraviolet ray irradiation and post exposure baking (PEE), a difference in solubility against a developing solution between the exposed part and the unexposed part is generated. One kind of the non-ionic photoacid generator (A) can be used alone or two or more kinds thereof can be used in combination.

Examples of the resin composition (Q) for photolithography include a mixture of a negative type chemical amplification resin (QN) and a non-ionic photoacid generator (A); and a mixture of a positive type chemical amplification resin (QP) and a non-ionic photoacid generator (A).

The negative type chemical amplification resin (QN) may be constituted of a phenolic hydroxyl group-containing resin (QN1) and a crosslinking agent (QN2).

No particular restriction is put on the phenolic hydroxyl group-containing resin (QN1) as long as the resin is a resin containing a phenolic hydroxyl group, and for example, a novolak resin, polyhydroxystyrene, a copolymer of hydroxystyrene, a copolymer of hydroxystyrene and styrene, a copolymer of hydroxystyrene, styrene and a (meth)acrylic acid derivative, a phenol-xylylene glycol condensation resin, a cresol-xylylene glycol condensation resin, a polyimide containing a phenolic hydroxyl group, a polyamic acid containing a phenolic hydroxyl group, a phenol-dicyclopentadiene condensation resin, and the like can be used. Of these, preferred are a novolak resin, polyhydroxystyrene, a copolymer of hydroxystyrene, a copolymer of hydroxystyrene and styrene, a copolymer of hydroxystyrene, styrene and a (meth)acrylic acid derivative, and a phenol-xylylene glycol condensation resin. In this connection, one kind of these phenolic hydroxyl group-containing resins (QN1) may be used alone and two or more kinds thereof may be mixedly used.

For example, the above-described novolak resin can be obtained by allowing a kind of phenol and a kind of aldehyde to undergo a condensation in the presence of a catalyst.

Examples of the above-described kind of phenol include phenol, o-cresol, m-cresol, p-cresol, o-ethylphenol, m-ethylphenol, p-ethylphenol, o-butylphenol, m-butylphenol, p-butylphenol, 2,3-xylenol, 2,4-xylenol, 2,5-xylenol, 2,6-xylenol, 3,4-xylenol, 3,5-xylenol, 2,3,5-trimethylphenol, 3,4,5-trimethylphenol, catechol, resorcinol, pyrogallol, α-naphthol, β-naphthol and the like.

Moreover, examples of the above-described kind of aldehyde include formaldehyde, paraformaldehyde, acetaldehyde, benzaldehyde and the like.

Specific examples of the novolak resin include a phenol/formaldehyde condensation novolak resin, a cresol/formaldehyde condensation novolak resin, a phenol-naphthol/formaldehyde condensation novolak resin, and the like.

Moreover, in the above-described phenolic hydroxyl group-containing resin (QN1), a phenolic low-molecular compound may be contained as one part of the components.

Examples of the above-described phenolic low-molecular compound include 4,4'-dihydroxydiphenylmethane, 4,4'-dihydroxydiphenylether, tris(4-hydroxyphenyl)methane, 1,1-bis(4-hydroxyphenyl)-1-phenylethane, tris(4-hydroxyphenyl)ethane, 1,3-bis[1-(4-hydroxyphenyl)-1-methylethyl]benzene, 1,4-bis[1-(4-hydroxyphenyl)-1-methylethyl]benzene, 4,6-bis[1-(4-hydroxyphenyl)-1-methylethyl]-1,3-dihydroxybenzene, 1,1-bis(4-hydroxyphenyl)-1-[4-[1-(4-hydroxyphenyl)-1-methylethyl]phenyl]ethane, 1,1,2,2-tetra(4-hydroxyphenyl)ethane, 4,4'-{1-[4-[1-(4-hydroxyphenyl)-1-methylethyl]phenyl]ethylidene}bisphenol, and the like. One kind of these phenolic low-molecular compounds may be used alone and two or more kinds thereof may be mixedly used.

The proportion of this phenolic low-molecular compound contained in the phenolic hydroxyl group-containing resin (QN1) is preferably 40% by weight or less, and more preferably 1 to 30% by weight, in the case where the amount of the phenolic hydroxyl group-containing resin (QN1) is defined as 100% by weight.

From the viewpoints of the resolution characteristics, thermal shock resistance, heat resistance, residual film ratio, and the like of the resulting insulation film, the weight-average molecular weight of the phenolic hydroxyl group-containing resin (QN1) is preferably 2000 or more, and more preferably 2000 to 20000 or so.

Moreover, the proportion of the phenolic hydroxyl group-containing resin (QN1) contained in a negative type chemical amplification resin (QN) is preferably 30 to 90% by weight, and more preferably 40 to 80% by weight, in the case where the whole composition excluding the solvent is defined as 100% by weight. In the case where the proportion of this phenolic hydroxyl group-containing resin (QN1) contained is 30 to 90% by weight, it is preferred because a film formed with a photosensitive insulation resin composition has a sufficient developability in an aqueous alkali solution.

The crosslinking agent (QN2) is not particularly limited as long as the crosslinking agent is a compound capable of allowing the phenolic hydroxyl group-containing resin (QN1) to be crosslinked by a strong acid generated from the non-ionic photoacid generator (A).

Examples of the crosslinking agent (QN2) include a bisphenol A-based epoxy compound, a bisphenol F-based epoxy compound, a bisphenol S-based epoxy compound, a novolak resin-based epoxy compound, a resole resin-based epoxy compound, a poly(hydroxystyrene)-based epoxy compound, an oxetane compound, a methylol group-containing melamine compound, a methylol group-containing benzoguanamine compound, a methylol group-containing urea compound, a methylol group-containing phenol compound, an alkoxyalkyl group-containing melamine compound, an alkoxyalkyl group-containing benzoguanamine compound, an alkoxyalkyl group-containing urea compound, an alkoxyalkyl group-containing phenol compound, a carboxymethyl group-containing melamine resin, a carboxymethyl group-containing benzoguanamine resin, a carboxymethyl group-containing urea resin, a carboxymethyl group-containing phenol resin, a carboxymethyl group-containing melamine compound, a carboxymethyl group-containing benzoguanamine compound, a carboxymethyl group-containing urea compound, a carboxymethyl group-containing phenol compound, and the like.

Among these crosslinking agents (QN2), preferred are a methylol group-containing phenol compound, a methoxymethyl group-containing melamine compound, a methoxymethyl group-containing phenol compound, a methoxymethyl group-containing glycoluril compound, a methoxymethyl group-containing urea compound and an acetoxymethyl group-containing phenol compound, and further preferred are a methoxymethyl group-containing melamine compound (for example, hexamethoxymethylmelamine or the like), a methoxymethyl group-containing glycoluril compound, a methoxymethyl group-containing urea compound, and the like. The methoxymethyl group-containing melamine compound is commercially available under the trade name of CYMEL 300, CYMEL 301, CYMEL 303, CYMEL 305 (available from MITSUI CYANAMID Co., Ltd.) or the like, the methoxymethyl group-containing glycoluril compound is commercially available under the trade name of CYMEL 1174 (available from MITSUI CYANAMID Co., Ltd.) or the like, and moreover, the methoxymethyl group-containing urea compound is commercially available under the trade name of MX290 (available from SANWA CHEMICAL CO., LTD.) or the like.

From the viewpoints of the lowering in the residual film ratio, the pattern meandering, the pattern swelling and the developability, the content of the crosslinking agent (QN2) is usually 5 to 60% by mole, preferably 10 to 50% by mole, and further preferably 15 to 40% by mole, relative to the whole amount of acidic functional groups in the phenolic hydroxyl group-containing resin (QN1).

Examples of the positive type chemical amplification resin (QP) include a protecting group-introduced resin (QP2) prepared by allowing one part or all of hydrogen atoms of the acidic functional group in an alkali-soluble resin (QP1) containing one kind or more of acidic functional groups such as a phenolic hydroxyl group, a carboxyl group, and a sulfonyl group to be substituted by acid-dissociable groups.

In this connection, the acid-dissociable group is a group capable of being dissociated in the presence of a strong acid generated from the non-ionic photoacid generator (A).

The protecting group-introduced resin (QP2) is alkali-insoluble or hardly alkali-soluble in itself.

Examples of the alkali-soluble resin (QP1) include a phenolic hydroxyl group-containing resin (QP11), a carboxyl group-containing resin (QP12), a sulfonic acid group-containing resin (QP13) and the like.

As the phenolic hydroxyl group-containing resin (QP11), one that is the same as the above-described phenolic hydroxyl group-containing resin (QN1) can be used.

No particular restriction is put on the carboxyl group-containing resin (QP12) as long as the resin is a polymer having a carboxyl group, and for example, the resin can be obtained by allowing a carboxyl group-containing vinyl monomer (Ba) and an optional hydrophobic group-containing vinyl monomer (Bb) to undergo a vinyl polymerization.

Examples of the carboxyl group-containing vinyl monomer (Ba) include an unsaturated monocarboxylic acid [such as (meth)acrylic acid, crotonic acid and cinnamic acid], an unsaturated polyvalent (di- to tetravalent) carboxylic acid [such as maleic acid (maleic anhydride), itaconic acid, fumaric acid and citraconic acid], an unsaturated polycarboxylic acid alkyl (an alkyl group with 1 to 10 carbon atoms) ester [such as a maleic acid monoalkyl ester, a fumaric acid monoalkyl ester and a citraconic acid monoalkyl ester], and a salt thereof [such as an alkali metal salt (a sodium salt, a potassium salt and the like), an alkaline earth metal salt (a calcium salt, a magnesium salt and the like), an amine salt and an ammonium salt].

Among these, from the viewpoints of the polymerizability and easy availability, preferred is an unsaturated monocarboxylic acid, and further preferred is a (meth)acrylic acid.

Examples of the hydrophobic group-containing vinyl monomer (Bb) include a (meth)acrylic acid ester (Bb1), an aromatic hydrocarbon monomer (Bb2) and the like.

Examples of the (meth)acrylic acid ester (Bb1) include an alkyl (meth)acrylate bearing an alkyl group with 1 to 20 carbon atoms [such as methyl (meth)acrylate, ethyl (meth)acrylate, n-propyl (meth)acrylate, isopropyl (meth)acrylate, n-butyl (meth)acrylate, n-hexyl (meth)acrylate and 2-ethylhexyl (meth)acrylate], an alicyclic group-containing (meth)acrylate [such as dicyclopentanyl (meth)acrylate, dicyclopentenyl (meth)acrylate and isobornyl (meth)acrylate] and the like.

Examples of the aromatic hydrocarbon monomer (Bb2) include a hydrocarbon monomer having a styrene skeleton [such as styrene, α-methylstyrene, vinyltoluene, 2,4-dimethylstyrene, ethylstyrene, isopropylstyrene, butylstyrene, phenylstyrene, cyclohexylstyrene and benzylstyrene], vinylnaphthalene and the like.

The charged monomer mole ratio of (Ba)/(Bb) in the carboxyl group-containing resin (QP12) is usually 10 to 100/0 to 90, from the viewpoint of the developability, preferably 10 to 80/20 to 90, and further preferably 25 to 85/15 to 75.

No particular restriction is put on the sulfonic acid group-containing resin (QP13) as long as the resin is a polymer having a sulfonic acid group, and for example, the resin can be obtained by allowing a sulfonic acid group-containing vinyl monomer (Bc) and an optional hydrophobic group-containing vinyl monomer (Bb) to undergo a vinyl polymerization.

As the hydrophobic group-containing vinyl monomer (Bb), one that is the same as the above-described one can be used.

Examples of the sulfonic acid group-containing vinyl monomer (Bc) include vinylsulfonic acid, (meth)allylsulfonic acid, styrenesulfonic acid, α-methylstyrenesulfonic acid, 2-(meth)acryloylamido-2-methylpropane sulfonic acid, and a salt thereof. Examples of the salt include an alkali metal (sodium, potassium or the like) salt, an alkaline earth metal (calcium, magnesium or the like) salt, a primary to tertiary amine salt, an ammonium salt, a quaternary ammonium salt, and the like.

The charged monomer mole ratio of (Bc)/(Bb) in the sulfonic acid group-containing resin (QP13) is usually 10 to 100/0 to 90, from the viewpoint of the developability, preferably 10 to 80/20 to 90, and further preferably 25 to 85/15 to 75.

With regard to the HLB value of the alkali-soluble resin (QP1), although the preferred range varies depending on the resin skeleton of the alkali-soluble resin (QP1), the HLB value preferably lies within the range of 4 to 19, further preferably lies within the range of 5 to 18, and especially preferably lies within the range of 6 to 17.

When the HLB value lies within the range of 4 or more, the developability is further improved at the time of performing developing, and when the HLB value lies within the range of 19 or less, the water resistance of a cured material is further improved.

In this connection, the HLB in the present invention refers to an HLB value according to the Oda method and refers to the hydrophilicity-hydrophobicity balance value, and the HLB can be calculated from the ratio of the organicity value and the inorganicity value of an organic compound.

$$HLB \approx 10 \times Inorganicity/Organicity$$

Moreover, the inorganicity value and the organicity value are described in detail in the document "Kaimen kasseizai no gosei to sono oyo" (published by MAKI SYOTEN, written by ODA, TERAMURA) p. 501; or "Shin●Kaimen kasseizai nyumon" (Takehiko FUJIMOTO, published by Sanyo Chemical Industries, Ltd.) p. 198.

For example, the acid-dissociable group in the protecting group-introduced resin (QP2) can be exemplified by a substituted methyl group, a 1-substituted ethyl group, a 1-branched alkyl group, a silyl group, a germyl group, an alkoxycarbonyl group, an acyl group, a cyclic acid-dissociable group, or the like. One kind of these may be used alone, and two or more kinds thereof may be used in combination.

For example, the substituted methyl group can be exemplified by a methoxymethyl group, a methylthiomethyl group, an ethoxymethyl group, an ethylthiomethyl group, a methoxyethoxymethyl group, a benzyloxymethyl group, a benzylthiomethyl group, a phenacyl group, a bromophenacyl group, a methoxyphenacyl group, a methylthiophenacyl group, an a-methylphenacyl group, a cyclopropylmethyl group, a benzyl group, a diphenylmethyl group, a triphenylmethyl group, a bromobenzyl group, a nitrobenzyl group, a methoxybenzyl group, a methylthiobenzyl group, an ethoxybenzyl group, an ethylthiobenzyl group, a piperonyl group, a methoxycarbonylmethyl group, an ethoxycarbonylmethyl group, an n-propoxycarbonylmethyl group, an i-propoxycarbonylmethyl group, an n-butoxycarbonylmethyl group, a tert-butoxycarbonylmethyl group, or the like.

For example, the 1-substituted ethyl group can be exemplified by a 1-methoxyethyl group, a 1-methylthioethyl group, a 1,1-dimethoxyethyl group, a 1-ethoxyethyl group, a 1-ethylthioethyl group, a 1,1-diethoxyethyl group, a 1-ethoxypropyl group, a 1-propoxyethyl group, a 1-cyclohexyloxyethyl group, a 1-phenoxyethyl group, a 1-phenylthioethyl group, a 1,1-diphenoxyethyl group, a 1-benzyloxyethyl group, a 1-benzyithioethyl group, a 1-cyclopropylethyl group, a 1-phenylethyl group, a 1,1-diphenylethyl group, a 1-methoxycarbonylethyl group, a 1-ethoxycarbonylethyl group, a 1-n-propoxycarbonylethyl group, a 1-isopropoxycarbonylethyl group, a 1-n-butoxycarbonylethyl group, a 1-tert-butoxycarbonylethyl group, or the like.

For example, the 1-branched alkyl group can be exemplified by an i-propyl group, a sec-butyl group, a tert-butyl group, 1,1-dimethylpropyl group, 1-methylbutyl group, 1,1-dimethylbutyl group, or the like.

For example, the silyl group can be exemplified by a tricarbylsilyl group such as a trimethylsilyl group, an ethyldimethylsilyl group, a methyldiethylsilyl group, a triethylsilyl group, an i-propyldimethylsilyl group, a methyldi-i-propylsilyl group, a tri-i-propylsilyl group, a tert-butyldimethylsilyl group, a methyldi-tert-butylsilyl group, a tri-tert-butylsilyl group, a phenyldimethylsilyl group, a methyldiphenylsilyl group and a triphenylsilyl group.

For example, the germyl group can be exemplified by a tricarbylgermyl group such as a trimethylgermyl group, an ethyldimethylgermyl group, a methyldiethylgermyl group, a triethylgermyl group, an isopropyldimethylgermyl group, a methyldi-i-propylgermyl group, a tri-i-propylgermyl group, a tert-butyldimethylgermyl group, a methyldi-tert-butylgermyl group, a tri-tert-butylgermyl group, a phenyldimethylgermyl group, a methyldiphenylgermyl group and a triphenylgermyl group.

For example, the alkoxycarbonyl group can be exemplified by a methoxycarbonyl group, an ethoxycarbonyl group, an i-propoxycarbonyl group, a tert-butoxycarbonyl group, or the like.

For example, the acyl group can be exemplified by an acetyl group, a propionyl group, a butyryl group, a heptanoyl group, a hexanoyl group, a valeryl group, a pivaloyl group, an isovaleryl group, a lauroyl group, a myristoyl group, a palmitoyl group, a stearoyl group, an oxalyl group, a malonyl group, a succinyl group, a glutaryl group, an adipoyl group, a pimeloyl group, a suberoyl group, an azelaoyl group, a sebacoyl group, an acryloyl group, a propioloyl group, a methacryloyl group, a crotonoyl group, an oleoyl group, a maleoyl group, a fumaroyl group, a mesaconoyl group, a campholoyl group, a benzoyl group, a phthaloyl group, an isophthaloyl group, a terephthaloyl group, a naphthoyl group, a toluoyl group, a hydroatropoyl group, an atropoyl group, a cinnamoyl group, a furoyl group, a thenoyl group, a nicotinoyl group, an isonicotinoyl group, a p-toluenesulfonyl group, a mesyl group, or the like.

For example, the cyclic acid-dissociable group can be exemplified by a cyclopropyl group, a cyclopentyl group, a cyclohexyl group, a cyclohexenyl group, a 4-methoxycyclohexyl group, a tetrahydropyranyl group, a tetrahydrofuranyl group, a tetrahydrothiopyranyl group, a tetrahydrothiofuranyl group, a 3-buromotetrahydropyranyl group, a 4-methoxytetrahydropyranyl group, a 4-methoxytetrahydrothiopyranyl group, 3-tetrahydrothiophene-1,1-dioxide, or the like.

Among these acid-dissociable groups, preferred are a tert-butyl group, a benzyl group, a 1-methoxyethyl group, a 1-ethoxyethyl group, a trimethylsilyl group, a tert-butoxycarbonyl group, a tert-butoxycarbonylmethyl group, a tetrahydropyranyl group, a tetrahydrofuranyl group, a tetrahydrothiopyranyl group, a tetrahydrothiofuranyl group, and the like.

Although the introduction ratio of the acid-dissociable group in the protecting group-introduced resin (QP2) {the proportion of the number of acid-dissociable groups to the total number of nonprotected acidic functional groups and acid-dissociable groups in the protecting group-introduced resin (QP2)} cannot be decided sweepingly according to the kind of an acid-dissociable group or an alkali-soluble resin into which the group is introduced, the introduction ratio is preferably 10 to 100%, and further preferably 15 to 100%.

With regard to the protecting group-introduced resin (QP2), the weight-average molecular weight in terms of polystyrene (hereinafter, referred to as "Mw") measured by gel permeation chromatography (GPC) is preferably 1,000 to 150,000, and further preferably 3,000 to 100,000.

Moreover, with regard to the protecting group-introduced resin (QP2), the ratio of the Mw to the number-average molecular weight in terms of polystyrene (hereinafter, referred to as "Mn") measured by gel permeation chromatography (GPC) (Mw/Mn) is usually 1 to 10, and preferably 1 to 5.

The content of the non-ionic photoacid generator (A) based on the weight of the solid content of the resin composition (Q) for photolithography is preferably 0.001 to 20% by weight, further preferably 0.01 to 15% by weight, and especially preferably 0.05 to 7% by weight.

When the content is 0.001% by weight or more, the sensitivity to ultraviolet rays can be further satisfactorily exhibited, and when the content is 20% by weight or less, the physical properties of a part insoluble to an alkali developing solution can be further satisfactorily exhibited.

For example, a resist prepared with the resin composition (Q) for photolithography according to the present invention can be formed by applying a resin solution prepared by dissolving the resin in a prescribed organic solvent (by dissolving the resin and dispersing inorganic fine particles in the case where the inorganic fine particles are included) on a substrate using a known method such as spin coating, curtain coating, roll coating, spray coating and screen printing, and then, allowing the solvent to be dried by heating or hot air blasting.

The organic solvent allowing the resin composition (Q) for photolithography to be dissolved therein is not particularly limited as long as the solvent is one capable of dissolving the resin composition therein and adjusting the physical properties (viscosity and the like) of the resin solution within an applicable range for spin coating or the like. For example, a known solvent such as N-methylpyrrolidone, N,N-dimethylformamide, dimethyl sulfoxide, toluene, ethanol, cyclohexanone, methanol, methyl ethyl ketone, ethyl acetate, butyl acetate, ethyl lactate, propylene glycol monomethyl ether acetate, acetone and xylene can be used.

Among these solvents, from the viewpoints of the drying temperature and the like, preferred is one with a boiling point of 200° C. or lower (toluene, ethanol, cyclohexanone, methanol, methyl ethyl ketone, ethyl acetate, butyl acetate, ethyl lactate, propylene glycol monomethyl ether acetate, acetone and xylene), and moreover, these solvents can be used alone or in combination of two or more kinds thereof.

In the case of using an organic solvent, although the amount of the solvent blended is not particularly limited, the amount thereof blended is usually preferably 30 to 1,000% by weight, further preferably 40 to 900% by weight, and especially preferably 50 to 800% by weight, on the basis of the weight of the solid content of the resin composition (Q) for photolithography.

Although the drying condition for the resin solution after being applied varies with the kind of a solvent to be used, the drying is performed preferably within a range of 50 to 200° C. and a range of 2 to 30 minutes, and the drying condition is appropriately determined in view of the amount (% by weight) of a residual solvent in the resin composition (Q) for photolithography after being dried, and the like.

A resist is formed on a substrate, after which photoirradiation corresponding to a wiring pattern shape is performed. Afterward, post exposure baking (PEB) is performed, and then, alkali development is performed to form the wiring pattern.

Examples of a method for performing photoirradiation include a method of performing exposure of a resist by means of an active light beam via a photomask having a wiring pattern. No particular restriction is put on the active light beam used for photoirradiation as long as the non-ionic photoacid generator (A) in the resin composition (Q) for photolithography according to the present invention can be decomposed.

Examples of the active light beam include a low pressure mercury lamp, a middle pressure mercury lamp, a high pressure mercury lamp, an ultra-high pressure mercury lamp, a xenon lamp, a metal halogen lamp, an electron beam irradiation device, an X-ray irradiation device, a laser (an argon laser, a dye laser, a nitrogen laser, an LED, a helium-cadmium laser, or the like) and the like. Among these, preferred are a high pressure mercury lamp and an ultra-high pressure mercury lamp.

The temperature at the time of post exposure baking (PEB) is usually 40 to 200° C., preferably 50 to 190° C., and further preferably 60 to 180° C. When the temperature is lower than 40° C., since the deprotective reaction or the crosslinking reaction does not proceed sufficiently, the difference in solubility between the ultraviolet ray-irradiated part and the ultraviolet ray-unirradiated part is too small to form a pattern, and when the temperature is higher than 200° C., there is a problem that the productivity is lowered.

The heating time is usually 0.5 to 120 minutes, and is preferably 1 to 90 minutes and further preferably 2 to 90 minutes. When the time is shorter than 0.5 minute, it is difficult to control the time and the temperature, and when the time is longer than 120 minutes, there is a problem that the productivity is lowered.

Examples of a method for performing alkali development include a method of removing a part to be dissolved by means of an alkali developing solution so as to form a wiring pattern. No particular restriction is put on the alkali developing solution as long as a condition of creating a difference in solubility between the ultraviolet ray-irradiated part and the ultraviolet ray-unirradiated part of the resin composition (Q) for photolithography can be attained.

Examples of the alkali developing solution include an aqueous sodium hydroxide solution, an aqueous potassium hydroxide solution, an aqueous solution of sodium bicarbonate and a tetramethylammonium salt, and the like.

These alkali developing solutions may be added with a water-soluble organic solvent. Examples of the water-soluble organic solvent include methanol, ethanol, isopropyl alcohol, tetrahydrofuran, N-methylpyrrolidone and the like.

Although examples of a developing method include a dip system, a shower system and a spray system using an alkali developing solution, more preferred is a spray system.

With regard to the temperature of a developing solution, the developing solution is used preferably at 25 to 40° C. The developing time is appropriately determined according to the thickness of a resist.

EXAMPLES

Hereinafter, the present invention will be further described by reference to examples and comparative examples, but the present invention should not be limited thereto. Hereinafter, % refers to % by weight and a part refers to a part by weight unless otherwise specified.

Example 1

<Synthesis of Non-Ionic Photoacid Generator (A-1)>

[Chemical 9]

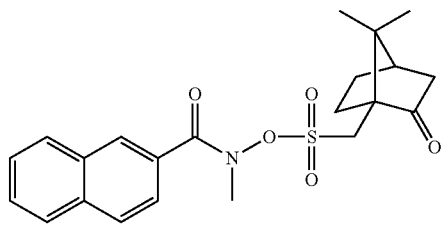

In methanol (50 mL), 8.3 g (0.100 mol) of N-methyl hydroxylammonium hydrochloride was dissolved, and to this solution, 60 g of a methanolic 10% potassium hydroxide solution was added dropwise with stirring at 0° C. Furthermore, a solution prepared by dissolving 9.5 g (0.050 mol) of 2-naphthoyl chloride in THF (35 mL) was added thereto, and the contents were stirred for 1 hour. The temperature of the reaction liquid was returned to room temperature, and furthermore, the contents were stirred for 1 hour, after which the solvent was distilled off by means of an evaporator. The residue was extracted with ethyl acetate and a saturated saline solution, and the organic layer was separated, after which the solvent was distilled off by means of an evaporator to recover white solid matter.

In chloroform (50 ml), 2.0 g of the obtained solid matter and 3.8 g (0.015 mol) of (+)-10-camphorsulfonyl chloride were dissolved, and into this solution, 3.4 g (0.015 mol) of pyridine was added dropwise and charged with stirring at 0° C. After being stirred for 8 hours at 50° C., this reaction liquid was extracted with chloroform-water, after which the organic layer was subjected to distillation under reduced pressure and the solvent was removed to obtain a brown oily substance. Furthermore, the oily substance was recrystallized from methanol to obtain 3.0 g (0.007 mol) of a sulfonate compound [Non-ionic photoacid generator (A-1)] represented by the above formula.

Example 2

<Synthesis of Non-Ionic Photoacid Generator (A-2)>

[Chemical 10]

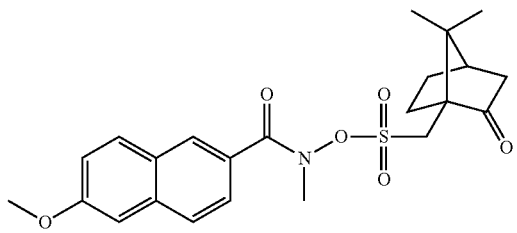

In thionyl chloride (100 mL), 20.2 g (0.100 mol) of 5-methoxy-2-naphthoic acid was dissolved, and the solution was stirred for 2 hours at 80° C. Then, the thionyl chloride and hydrochloric acid generated in the system were distilled off under reduced pressure at 80° C. to obtain 20.0 g (0.090 mol) of 5-methoxy-2-naphthoyl chloride.

After that, the operation was performed in the same manner as that in Example 1 except that 9.5 g (0.050 mol) of 2-naphthoyl chloride was changed to 11.0 g (0.050 mol) of 5-methoxy-2-naphthoyl chloride, and a sulfonate compound [Non-ionic photoacid generator (A-2)] represented by the above formula was obtained.

Example 3

<Synthesis of Non-Ionic Photoacid Generator (A-3)>

[Chemical 11]

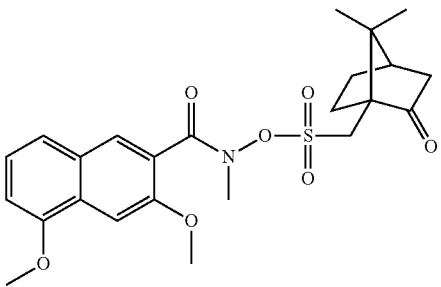

In acetone (120 mL), 10.3 g (0.100 mol) of 3,5-dihydroxynaphthoic acid was dissolved, and to this solution, 83.6 g (0.605 mol) of potassium carbonate and 28.4 g (0.221 mol) of dimethyl sulfate were added, and the contents were stirred for 12 hours at 50° C. The reaction liquid was filtered to remove solid matter, after which the solvent was distilled off by means of an evaporator, and then, water (50 mL), methanol (50 mL) and potassium hydroxide (10 g) were added thereto, and the contents were stirred for 3 hours at 65° C. To the contents, 100 g of hydrochloric acid was added, and the precipitated solid matter was recovered to obtain 20.0 g (0.087 mol) of 3,5-dimethoxy-2-naphthoic acid.

In thionyl chloride (100 mL), 20.0 g (0.087 mol) of 3,5-dimethoxy-2-naphthoic acid thus obtained was dissolved, and the solution was stirred for 2 hours at 80° C. Then, the thionyl chloride and hydrochloric acid generated in the system were distilled off under reduced pressure at 80° C. to obtain 20.0 g (0.083 mol) of 3,5-dimethoxy-2-naphthoyl chloride.

After that, the operation was performed in the same manner as that in Example 1 except that 9.5 g (0.050 mol) of 2-naphthoyl chloride was changed to 11.8 g (0.050 mol) of 3,5-dimethoxy-2-naphthoyl chloride, and a sulfonate compound [Non-ionic photoacid generator (A-3)] represented by the above formula was obtained.

Example 4

<Synthesis of Non-Ionic Photoacid Generator (A-4)>

[Chemical 12]

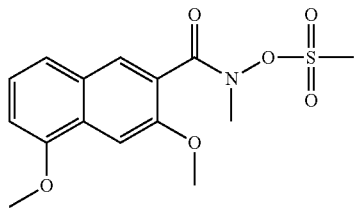

In acetone (120 mL), 10.3 g (0.100 mol) of 3,5-dihydroxynaphthoic acid was dissolved, and to this solution, 83.6 g (0.605 mol) of potassium carbonate and 28.4 g (0.221 mol) of dimethyl sulfate were added, and the contents were stirred for 12 hours at 50° C. The reaction liquid was filtered to remove solid matter, after which the solvent was distilled off by means of an evaporator, and then, water (50 mL), methanol (50 mL) and potassium hydroxide (10 g) were added thereto, and the contents were stirred for 3 hours at 65° C. To the contents, 100 g of hydrochloric acid was added, and the precipitated solid matter was recovered to obtain 20.0 g (0.087 mol) of 3,5-dimethoxy-2-naphthoic acid.

In thionyl chloride (100 mL), 20.0 g (0.087 mol) of 3,5-dimethoxy-2-naphthoic acid thus obtained was dissolved, and the solution was stirred for 2 hours at 80° C. Then, the thionyl chloride and hydrochloric acid generated in the system were distilled off under reduced pressure at 80° C. to obtain 20.0 g (0.083 mol) of 3,5-dimethoxy-2-naphthoyl chloride.

In methanol (50 mL), 8.3 g (0.100 mol) of N-methyl hydroxylammonium hydrochloride was dissolved, and to this solution, 60 g of a methanolic 10% potassium hydroxide solution was added dropwise with stirring at 0° C. Furthermore, a solution prepared by dissolving 9.5 g (0.050 mol) of 2-naphthoyl chloride in THF (35 mL) was added thereto, and the contents were stirred for 1 hour. The temperature of the reaction liquid was returned to room temperature, and furthermore, the contents were stirred for 1 hour, after which the solvent was distilled off by means of an evaporator. The residue was extracted with ethyl acetate and a saturated saline solution, and the organic layer was separated, after which the solvent was distilled off by means of an evaporator to recover white solid matter.

In chloroform (50 ml), 2.0 g of the obtained white solid matter and 1.8 g (0.015 mol) of methanesulfonic acid chloride were dissolved, and into this solution, 3.4 g (0.015 mol) of pyridine was added dropwise and charged with stirring at 0° C. After being stirred for 8 hours at 50° C., this reaction liquid was extracted with chloroform-water, after which the organic layer was subjected to distillation under reduced pressure and the solvent was removed to obtain a brown oily substance. Furthermore, the oily substance was recrystallized from methanol to obtain a sulfonate compound [Non-ionic photoacid generator (A-4)] (0.007 mol) represented by the above formula.

Example 5

<Synthesis of Non-Ionic Photoacid Generator (A-5)>

[Chemical 13]

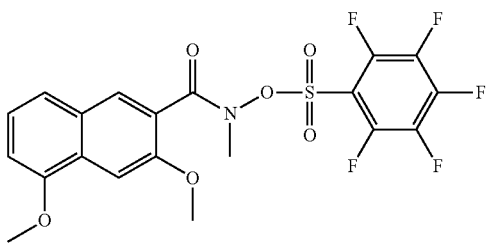

In chloroform (50 ml), 2.0 g of white solid matter obtained by the same process as that in Example 4 and 4.1 g (0.015 mol) of pentafluorobenzenesulfonic acid chloride were dissolved, and into this solution, 3.4 g (0.015 mol) of pyridine was added dropwise and charged with stirring at 0° C. After being stirred for 8 hours at 50° C., this reaction liquid was extracted with chloroform-water, after which the organic layer was subjected to distillation under reduced pressure and the solvent was removed to obtain a brown oily substance. Furthermore, the oily substance was recrystallized from methanol to obtain a sulfonate compound [Non-ionic photoacid generator (A-5)] (0.007 mol) represented by the above formula.

Example 6

<Synthesis of Non-Ionic Photoacid Generator (A-6)>

[Chemical 14]

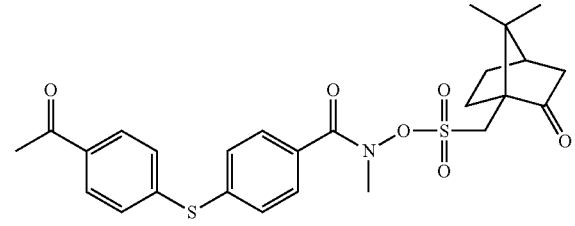

In N,N-dimethylformamide (340 mL), 14.1 g (0.128 mol) of thiophenol and 7.2 g (0.128 mol) of potassium hydroxide were dissolved, and the solution was stirred for 1 hour at 70° C. To this solution, 32 g (0.122 mol) of methyl 4-iodobenzoate and 1.2 g (0.006 mol) of copper(I) iodide were added, and the contents were stirred for 12 hours at 160° C. After the temperature of the reaction liquid was returned to room temperature, solid matter precipitated by the addition of hydrochloric acid was recovered and washed with 2-propanol to obtain 24 g (0.104 mol) of 4-thiophenylbenzoic acid.

In dichloromethane (200 mL), 9.8 g (0.125 mol) of acetyl chloride and 33.3 g (0.250 mol) of aluminum chloride were dissolved, and to this solution, a dichloromethane solution (36 mL) of 24 g (0.104 mol) of 4-thiophenylbenzoic acid was added dropwise with stirring at 0° C. After being stirred for 2 hours at room temperature, the liquid was charged into ice water, and furthermore, the contents were stirred for 1 hour. The precipitated solid matter was recovered and washed with an aqueous sodium hydroxide solution and methanol to obtain 24 g (0.087 mol) of 4-thio(4-acetylphenyl)benzoic acid.

In thionyl chloride (100 mL), 24 g (0.087 mol) of 4-thio (4-acetylphenyl)benzoic acid thus obtained was dissolved, and the solution was stirred for 2 hours at 80° C. Then, the thionyl chloride and hydrochloric acid generated in the system were distilled off under reduced pressure at 80° C. to obtain 23 g (0.083 mol) of 4-thio(4-acetylphenyl)benzoic acid chloride.

After that, the operation was performed in the same manner as that in Example 1 except that 9.5 g (0.050 mol) of 2-naphthoyl chloride was changed to 14.3 g (0.050 mol) of 4-thio(4-acetylphenyl)benzoic acid chloride, and a sulfonate compound [Non-ionic photoacid generator (A-6)] represented by the above formula was obtained.

Example 7

<Synthesis of Non-Ionic Photoacid Generator (A-7)>

[Chemical 15]

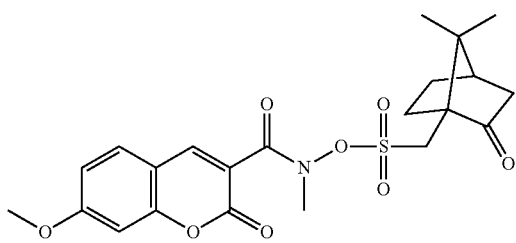

Into water, 19.0 g (0.125 mol) of 2-hydroxy-4-methoxybenzaldehyde was charged, and to this mixture, 23.4 g (0.162 mol) of Meldrum's acid was added with stirring. The contents were stirred for 2 hours at 100° C. under refluxing, after which the temperature of the contents was returned to room temperature to recover solid matter. The solid matter was washed with a mixed solvent of water and methanol to obtain 19.2 g (0.087 mol) of 7-methoxy-3-coumarinic acid.

In thionyl chloride (100 mL), 19.2 g (0.087 mol) of 7-methoxy-3-coumarinic acid was dissolved, and the solution was stirred for 2 hours at 80° C. Then, the thionyl chloride and hydrochloric acid generated in the system were distilled off under reduced pressure at 80° C. to obtain 19.9 g (0.083 mol) of 7-methoxy-3-coumarinic acid chloride.

After that, the operation was performed in the same manner as that in Example 1 except that 9.5 g (0.050 mol) of 2-naphthoyl chloride was changed to 12.0 g (0.050 mol) of 7-methoxy-3-coumarinic acid chloride, and a sulfonate compound [Non-ionic photoacid generator (A-7)] represented by the above formula was obtained.

Example 8

<Synthesis of Non-Ionic Photoacid Generator (A-8)>

[Chemical 16]

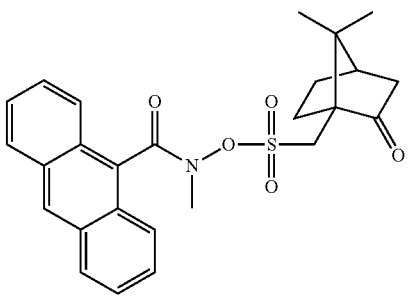

In thionyl chloride (0.100 mL), 19.5 g (0.087 mol) of 9-anthracenecarboxylic acid was dissolved, and the solution was stirred for 2 hours at 80° C. Then, the thionyl chloride and hydrochloric acid generated in the system were distilled off under reduced pressure at 80° C. to obtain 20.0 g (0.083 mol) of 9-anthracenecarboxylic acid chloride.

After that, the operation was performed in the same manner as that in Example 1 except that 9.5 g (0.050 mol) of 2-naphthoyl chloride was changed to 12.0 g (0.050 mol) of 9-anthracenecarboxylic acid chloride, and a sulfonate compound [Non-ionic photoacid generator (A-8)] represented by the above formula was obtained.

Comparative Example 1

<Synthesis of Non-Ionic Photoacid Generator (A'-1)>

[Chemical 17]

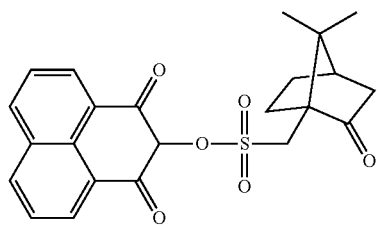

A mixture of naphthalic anhydride (3.0 g, 0.050 mmol), 4.9 g (0.070 mol) of hydroxylamine hydrochloride and pyridine (50 mL) was stirred for 10 hours at 100° C. After being cooled to room temperature, the reaction liquid was charged into 1 N hydrochloric acid, and the precipitate was recovered by filtration.

In pyridine (20 ml), 3.0 g of the obtained precipitate was dissolved, and into this solution, 37.5 g (0.150 mmol) of (+)-10-camphorsulfonyl chloride was added dropwise and charged with stirring at 0° C. After being stirred for 8 hours at 25° C., this reaction liquid was extracted with dichloromethane-water, after which the organic layer was subjected to distillation under reduced pressure and the solvent was removed to obtain an orange oily substance. Furthermore, the oily substance was recrystallized from methanol to obtain a compound [Non-ionic photoacid generator (A'-1)] (4.3 g, 0.010 mol) represented by the above formula.

Comparative Example 2

<Synthesis of Ionic Photoacid Generator (A'-2)>

[Chemical 18]

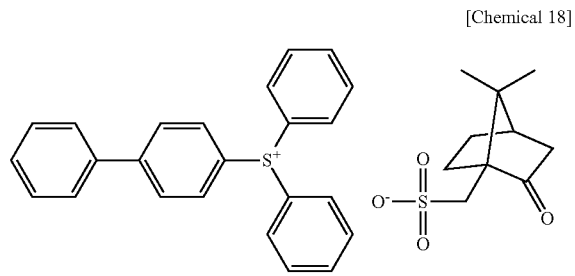 [SMILES: c1ccc(-c2ccc([S+](c3ccccc3)c3ccccc3)cc2)cc1 ; CC1(C)C2CCC1(CS(=O)(=O)[O-])C(=O)C2]

To a stirred mixture of 12.1 parts of diphenyl sulfoxide, 9.3 parts of diphenyl sulfide and 67.0 parts of (+)-10-camphorsulfonic acid, 7.9 parts of acetic anhydride was added dropwise, and the contents were allowed to undergo a reaction for 5 hours at 40 to 50° C., and then, cooled to 25° C. This reaction solution was charged into 121 parts of water and the contents were stirred for 8 hours at 50° C., whereupon a slightly viscous yellow oily substance was precipitated. This oily substance was extracted with ethyl acetate, the organic layer was washed several times with water, and then, the solvent was distilled off from the organic layer. The obtained residue was added with toluene to be dissolved therein, after which hexane was added to the solution, and the contents were thoroughly stirred for 1 hour at 10° C., and then, allowed to settle. After 1 hour, since the solution separated into two layers, the upper layer was removed by a liquid-liquid separation technique. The residual lower layer was added with hexane and the contents were thoroughly mixed at 25° C., whereupon pale yellow crystals were precipitated. The crystals were filtered off and dried under reduced pressure to obtain a compound [Ionic photoacid generator (A'-2)] represented by the above formula.

<Performance Evaluation>

With regard to the performance evaluation of the photoacid generator, obtained non-ionic photoacid generators (A-1) to (A-8), non-ionic photoacid generators (A'-1), and ionic photoacid generators (A'-2) were evaluated for the molar extinction coefficient, the resist curing properties, the thermal decomposition temperature and the solvent solubility in the following manner.

<Molar Extinction Coefficient>

The synthesized photoacid generator was diluted to 0.25 mmol/L with acetonitrile, and using an ultraviolet-visible spectrophotometer (UV-2550 available from SHIMADZU CORPORATION), the absorbance in a range of 200 nm to 500 nm was measured with a cell having an optical path length (a cell length) of 1 cm. The molar extinction coefficient of i-line (365 nm) ($\varepsilon_{365}$) was calculated from the following equation.

$$\varepsilon_{365}(\text{L·mol}^{-1}\cdot\text{cm}^{-1}) = A_{365}/(0.00025 \text{ mol/L} \times 1 \text{ cm})$$

[In the equation, $A_{365}$ represents the absorbance at 365 nm.]

<Resist Curing Properties>

A resin solution of 75 parts of a phenol resin ("PHENOLITE TD 431" available from DIC Corporation), 25 parts of a melamine curing agent ("CYMEL 300" available from MITSUI CYANAMID Co., Ltd.), 1 part of a synthesized photoacid generator and 200 parts of propylene glycol monomethyl ether acetate (hereinafter, abbreviated as PGMEA) was applied on a glass substrate of 10 cm square under a condition of 10 seconds at 1000 rpm using a spin coater. Then, the applied film was dried under vacuum for 5 minutes at 25° C., after which the film was dried for 3 minutes on an 80° C. hot plate to form a resist film with a film thickness of about 3 µm. The whole face of this resist film was exposed with a prescribed dose of ultraviolet light having a wavelength limited by the L-34 filter (a filter cutting light with a wavelength less than 340 nm, available from Kenko Optical Co., Ltd.) using an ultraviolet irradiation device (HMW-661F-01 available from ORC MANUFACTURING CO., LTD.). In this connection, a wavelength of 365 nm was measured for the integrated exposure quantity. Then, the film was subjected to post exposure baking (PEB) for 10 minutes with a 120° C. fair wind dryer, after which the film was immersed for 30 seconds in a 0.5% potassium hydroxide solution to be subjected to development, washed immediately with water and dried.

The film thickness of this resist film was measured using a shape measuring microscope (super-depth shape measuring microscope VK-8550, available from KEYENCE CORPORATION).

In this context, the resist curing properties were evaluated according to the following criteria on the basis of the lowest exposure quantity with which a change in film thickness of the resist film before and after development of within 10% was attained.

⊚: The lowest exposure quantity is 200 mJ/cm² or less.
○: The lowest exposure quantity is greater than 200 mJ/cm² and 300 mJ/cm² or less.
Δ: The lowest exposure quantity is greater than 300 mJ/cm² and 500 mJ/cm² or less.
×: The lowest exposure quantity is greater than 500 mJ/cm².

<Thermal Decomposition Temperature>

The synthesized photoacid generator was measured for the change in weight under a temperature increasing condition of 10° C./minute from 30° C. to 500° C. under a nitrogen atmosphere using a thermal gravimetric/differential thermal analyzer (TG/DTA 6200, available from Seiko Instruments Inc.), and a point where the weight was reduced by 2% was defined as the thermal decomposition temperature.

<Solvent Solubility>

In a test tube, 0.1 g of the synthesized photoacid generator was placed, and an organic solvent (butyl acetate, toluene or PGMEA) was added thereto in 0.2 g portions under a condition where the temperature was adjusted to 25° C. until the photoacid generator was completely dissolved. In this connection, in the case where the photoacid generator was not completely dissolved even when 20 g of the solvent was added, the photoacid generator was evaluated as one that was not dissolved.

The non-ionic photoacid generators (A-1) to (A-8) according to the present invention prepared in Examples, the non-ionic photoacid generators (A'-1) for comparison prepared in Comparative Examples 1 and ionic photoacid generators (A'-2) for comparison prepared in Comparative Examples 2 were measured for the molar extinction coefficient, the thermal decomposition temperature and the solvent solubility in the foregoing manner. The results are shown in Table 1.

TABLE 1

| | Example 1 | Example 2 | Example 3 | Example 4 | Example 5 |
|---|---|---|---|---|---|
| Photoacid generator | A-1 | A-2 | A-3 | A-4 | A-5 |
| Molar extinction coefficient (L · mol⁻¹ · cm⁻¹) | 80 | 120 | 360 | 300 | 400 |

TABLE 1-continued

| | | | | | |
|---|---|---|---|---|---|
| Resist curing properties | Δ | ○ | ◎ | ◎ | ◎ |
| Thermal decomposition temperature (° C.) | 230 | 225 | 225 | 225 | 225 |
| Solvent solubility (wt %) | Butyl acetate | 20 | 15 | 15 | 20 | 10 |
| | Toluene | 12 | 10 | 10 | 10 | 10 |
| | PGMEA | 20 | 15 | 15 | 20 | 10 |

| | Example 6 | Example 7 | Example 8 | Comparative Example 1 | Comparative Example 2 |
|---|---|---|---|---|---|
| Photoacid generator | A-6 | A-7 | A-8 | A'-1 | A'-2 |
| Molar extinction coefficient (L·mol⁻¹·cm⁻¹) | 450 | 6500 | 9000 | 330 | 80 |
| Resist curing properties | Δ | ○ | ○ | X | X |
| Thermal decomposition temperature (° C.) | 210 | 220 | 240 | 225 | 340 |
| Solvent solubility (wt %) Butyl acetate | 15 | 15 | 5 | 1 | <0.5 |
| Toluene | 10 | 10 | 10 | 0.5 | <0.5 |
| PGMEA | 15 | 15 | 5 | 0.5 | 15 |

As apparent from Table 1, it has been found that the non-ionic photoacid generators (A) in Examples 1 to 8 according to the present invention are excellent in resist curing properties and solubility to a solvent, also have a thermal decomposition temperature of 200° C. or more, and have sufficient stability.

On the other hand, in Comparative Example 1 where a conventionally known non-ionic photoacid generator is used and Comparative Example 2 where an ionic photoacid generator is used, it cannot be said that the resist curing properties are sufficient, and moreover, it has been found that the solubility to a solvent is insufficient.

INDUSTRIAL APPLICABILITY

The non-ionic photoacid generator (A) according to the present invention is suitable as a photoacid generator used for a positive type resist, a resist film, a liquid resist, a negative type resist, a resist for MEMS, a photosensitive material, a nanoimprint material, a material for microphotofabrication, or the like. Moreover, the resin composition (Q) for photolithography according to the present invention is suitably provided for above-described applications.

The invention claimed is:

1. A sulfonate compound of formula (1):

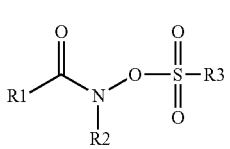

wherein in formula (1), R1 represents an aryl group selected from the group consisting of a naphthyl group, an anthracenyl group, and a coumarinyl group, in which R1 has a substituent when R1 is the naphthyl group and may have a substituent when R1 is any of the other groups, R2 represents a hydrogen atom, an alkyl group having 1 to 18 carbon atoms, an alkenyl group having 2 to 18 carbon atoms, an alkynyl group having 2 to 18 carbon atoms, or an aryl group having 6 to 18 carbon atoms, and R3 represents a linear alkyl group having 1 to 18 carbon atoms, a branched-chain alkyl group having 1 to 18 carbon atoms, a cycloalkyl group having 3 to 18 carbon atoms, or an aryl group having 6 to 10 carbon atoms, which can be substituted with fluorine.

2. The sulfonate compound according to claim 1, wherein, in formula (1), R2 is a hydrogen atom or an alkyl group having 1 to 18 carbon atoms.

3. A non-ionic photoacid generator, containing the sulfonate compound according to claim 1.

4. A resin composition for photolithography, containing the non-ionic photoacid generator according to claim 3.

5. The sulfonate compound according to claim 1, wherein the substituent is selected from the group consisting of an alkyl group, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, and a halogen atom.

6. The sulfonate compound according to claim 1, wherein the substituent is an alkoxy group.

* * * * *